(12) United States Patent
Alexander

(10) Patent No.: US 7,976,872 B2
(45) Date of Patent: Jul. 12, 2011

(54) METHOD FOR DISTRIBUTING A PHARMACEUTICALLY ACTIVE COMPOUND IN AN EXCIPIENT

(75) Inventor: Thomas A. Alexander, South Bend, IN (US)

(73) Assignee: L. Perrigo Company, Allegan, MI (US)

( * ) Notice: Subject to any disclaimer, the term of this patent is extended or adjusted under 35 U.S.C. 154(b) by 1387 days.

(21) Appl. No.: 11/491,844

(22) Filed: Jul. 24, 2006

(65) Prior Publication Data

US 2008/0020047 A1 Jan. 24, 2008

(51) Int. Cl.
*A61K 9/20* (2006.01)
*A61K 9/14* (2006.01)

(52) U.S. Cl. .................. 424/489; 424/464; 424/465

(58) Field of Classification Search .......... 424/465–480, 424/489
See application file for complete search history.

(56) References Cited

U.S. PATENT DOCUMENTS

| | | | |
|---|---|---|---|
| 3,048,526 A | 8/1962 | Boswell | |
| 4,358,207 A | 11/1982 | Roth | |
| 4,443,467 A * | 4/1984 | Ward | 514/428 |
| 5,470,603 A | 11/1995 | Staniforth et al. | |
| 5,507,573 A | 4/1996 | Hiorth | |
| 5,599,577 A | 2/1997 | Stevens et al. | |
| 5,716,641 A | 2/1998 | Stevens et al. | |
| 5,858,406 A * | 1/1999 | Stead et al. | 424/465 |
| 5,980,944 A | 11/1999 | Stevens et al. | |
| 6,074,688 A | 6/2000 | Pletcher et al. | |
| 6,117,479 A | 9/2000 | Hogan et al. | |
| 6,146,685 A | 11/2000 | Chrai et al. | |
| 6,177,125 B1 | 1/2001 | Voss | |
| 6,319,541 B1 | 11/2001 | Pletcher et al. | |
| 6,350,398 B1 * | 2/2002 | Breitenbach et al. | 264/129 |
| 6,397,840 B1 | 6/2002 | Chrai et al. | |
| 6,406,738 B1 | 6/2002 | Hogan et al. | |
| 6,623,785 B2 | 9/2003 | Childers | |
| 6,684,917 B2 | 2/2004 | Zhu et al. | |
| 6,764,720 B2 | 7/2004 | Pui et al. | |
| 6,806,017 B2 | 10/2004 | Reeves et al. | |
| 2002/0034592 A1 | 3/2002 | Hogan et al. | |
| 2002/0197388 A1 | 12/2002 | Brown et al. | |
| 2003/0113445 A1 | 6/2003 | Martin | |
| 2004/0052731 A1 * | 3/2004 | Hirsh et al. | 424/10.1 |
| 2004/0052847 A1 | 3/2004 | Namburi et al. | |
| 2004/0052938 A1 | 3/2004 | Feather et al. | |
| 2004/0063664 A1 | 4/2004 | Danielson et al. | |
| 2005/0129746 A1 | 6/2005 | Lee et al. | |

* cited by examiner

*Primary Examiner* — Michael G Hartley
*Assistant Examiner* — Micah-Paul Young
(74) *Attorney, Agent, or Firm* — Price, Heneveld, Cooper, DeWitt & Litton, LLP

(57) ABSTRACT

A process for uniformly distributing a pharmaceutically active particulate material in a pharmaceutically inert particulate material includes steps of providing a first layer of a pharmaceutically inert particulate material, disposing a layer of a pharmaceutically active particulate material on the first layer of pharmaceutically inert particulate material, passing the layers of particulate material through a static mixer, and discharging the blended mixture from the static mixer. The process is particularly useful for blending a low dose, high potency drug having a propensity to stick to process equipment surfaces with pharmaceutically inert particulate materials, such as diluents and/or excipients.

20 Claims, No Drawings

METHOD FOR DISTRIBUTING A PHARMACEUTICALLY ACTIVE COMPOUND IN AN EXCIPIENT

FIELD OF THE INVENTION

This invention relates to the manufacturing of solid dosage forms containing a physiologically active compound that is distributed in a physiologically inert material, such as an excipient or filler, and more particularly to processes for distributing, in an inert material, a physiologically active compound having a propensity to stick to process apparatus surfaces.

BACKGROUND OF THE INVENTION

Conventional methods of dispersing a high potency, low dose drug into a physiologically inert material that is subsequently processed into a solid oral dosage form have involved preparing a premix or granulation in which a portion of one or more of the physiologically inert materials is first combined with the physiologically active compound using a low shear mixing device, such as a twinshell blender, a double cone blender, or a drum roll mixer. The premix or granulation is then passed through a mill, such as a Fitzpatrick® Comminutor, to enhance homogeneity of the mixture. The milled material can then be blended with other materials to form a final product mixture that is compressed into a tablet, filled into a capsule, or otherwise incorporated into a solid oral dosage form.

A problem with conventional techniques of dispersing a high potency, low dose drug into physiologically inert materials is that certain pharmaceutically active low dose drugs, such as loperamide hydrochloride, have a high affinity for adhering to surfaces of process containers and equipment. As a result, while an acceptably uniform or homogeneous distribution of the drug in the inert materials can be achieved using conventional methods, there can be a loss of potency in the final product due to adherence of the drug to process equipment surfaces. Further, loss of the active compound on process equipment surfaces represents a waste of the active compound, and ultimately a higher production cost.

SUMMARY OF THE INVENTION

The invention provides a process for distributing a pharmaceutically active particulate material in a pharmaceutically inert particulate material which minimizes exposure of the pharmaceutically active material to production equipment surfaces.

The processes of this invention involve steps of providing a first layer of a pharmaceutically inert particulate material, disposing a layer of a pharmaceutically active particulate material on the first layer of pharmaceutically inert particulate material, passing the layers of particulate material through a static mixer, and discharging a blended mixture of the pharmaceutically active particulate material and the pharmaceutically inert particulate material.

These and other features, advantages and objects of the present invention will be further understood and appreciated by those skilled in the art by reference to the following specification and claims.

DETAILED DESCRIPTION OF PREFERRED EMBODIMENTS

Static mixers are mixing units that do not have any moving parts, such as mixing blades. Instead, static mixers include a series of mixing elements that are fixed within the mixer, generally a cylindrical or pipe-shaped apparatus. The mixer uses the energy of a flow stream to create mixing, typically between two or more fluids or between a solid and a fluid. Static mixers are commonly employed in the pulp and paper manufacturing industry, municipal water treatment, waste water treatment, power generation, at oil and gas wells, and in the chemicals, plastics and food industries. In the pharmaceutical industry, static mixers are most typically employed for blending liquid products.

Static mixers are well known in the art and generally comprise mixing elements that project from the walls of the mixing vessel, and which are configured and arranged in the vessel to cause mixing upon flow of materials through the vessel. Mixing involves a combination of material deflection and vortex generation, which induce turbulence and mixing.

While static mixers are not generally used for blending solid particulate materials, and while the uniformity or homogeneity of the resulting mixture of particulate materials passed through a static mixer generally is not superior to blends prepared using more conventional techniques, use of a static mixer has an advantage of minimizing contact or exposure of a high potency, low dosage drug with process equipment surfaces during the blending process.

A static mixing step can effectively replace a multiple step procedure involving mixing, collecting and milling that is conventionally used for blending dry particulate materials. Static mixing is particularly useful for low dosage drugs that have a propensity to adhere to process equipment surfaces, such as loperamide hydrochloride.

In general, the process involves layering a pharmaceutically active particulate material on a layer of a pharmaceutically inert particulate material which is to be blended with the active material. Typically, a plurality of alternating layers of a pharmaceutically inert particulate material and a pharmaceutically active particulate material are deposited in a hopper. The alternate layers of particulate material in the hopper are discharged into a static mixer, passed through the static mixer, and discharged as a blended mixture.

An example of a pharmaceutically active material that is administered in low doses and has a propensity to adhere to process equipment surfaces is loperamide hydrochloride. Loperamide hydrochloride is a high potency, low dose drug having a typical therapeutic dose of 2 milligrams. Uniform distribution of loperamide hydrochloride in a tablet mix and in the resulting compressed tablet is challenging for high potency drugs such as loperamide hydrochloride. Such drugs are typically prepared for tableting using a premix or granulation. For high potency drugs, a premix blend is prepared in which the pharmaceutically active ingredient is blended with a portion of the remaining ingredients (e.g., diluents and/or excipients). Premixes are typically prepared using low shear mixers, such as twinshell blenders, double cone blenders, or drum roll mixers. The premix is typically passed through a milling apparatus, such as a Fitzpatrick® Comminutor, to further mix the ingredients. The milled material can then be added to the remaining portion of the pharmaceutically inert ingredients (e.g., excipients and/or diluents) and further processed using a granulation technique. The granulation may then be mixed with any remaining ingredients in the formulation (e.g., tableting aids) prior to being compressed to form a final tablet product.

It is generally difficult to maintain predictability and/or consistency in the amount of low dose drugs, such as loperamide hydrochloride, that will adhere to process equipment surfaces. As a result, the amount of the active ingredient that is utilized in the formulation is the amount needed to achieve the required dose assuming that all ingredients will become part of the final product, i.e., that none of the ingredients remained adhered to process equipment surfaces. However, because this does not occur with certain drugs that have a tendency to stick to process equipment surfaces, the actual dose of the final tablet product is typically less than the targeted dosage.

An objection of the invention is to reduce contact between a low dose, high potency pharmaceutically active ingredient and process equipment surfaces during an initial mixing step by first layering the pharmaceutically active ingredient onto a layer of pharmaceutically inert material, or between layers of pharmaceutically inert material, such as in a hopper located adjacent to the mixing apparatus, and passing the layers through a static mixer which effectively disperses the pharmaceutically active ingredient into the pharmaceutically inert materials while minimizing contact of the pharmaceutically active ingredient with process equipment surfaces.

Preferably, the hopper is designed so that there will be multiple layers of drug disposed between layers of pharmaceutically inert materials (e.g., excipients and/or diluents). When the layered materials pass through the static mixer, the pharmaceutically active material is drawn through the pharmaceutically inert material and dispersed throughout the pharmaceutically inert material as it is discharged from the static mixer.

While the process of this invention was developed for uniformly distributing loperamide hydrochloride in pharmaceutically inert particulate materials in order to prevent adherence of the loperamide hydrochloride to process equipment surfaces, it is expected that the process will be useful for preparing other particulate mixtures for use in solid dosage forms, particularly, solid dosage forms containing a high potency, low dose drug having a propensity to adhere to process equipment surfaces. The invention is also expected to provide benefits for dispersing generally any pharmaceutically active particulate material into a pharmaceutically inert particulate material to achieve uniform mixing of the active material with the inert material, while eliminating multiple processing steps and handling steps. In particular, the process of the invention replaces conventional techniques involving preparation of premix blends, milling and granulation. However, the process is particularly advantageous for preparing uniform blends of pharmaceutically inert particulate materials with high potency drugs, such as those administered in tablets containing an active dose of 50 milligrams or less, more typically 20 milligrams or less, more preferably 10 milligrams or less, even more preferably 5 milligrams or less, and most preferably about 2 milligrams or less.

Typically, the pharmaceutically inert particulate materials are deposited into a hopper to form a first layer at the bottom of the hopper, and alternating layers of pharmaceutically active particulate material and pharmaceutically inert materials are added to the hopper to form a plurality of layers. Typically, the weight ratio of pharmaceutically inert particulate material in one layer to pharmaceutically active particulate material in an adjacent layer is from about 5:1 to about 50:1, and more preferably from about 5:1 to about 20:1.

The selection of materials for the layer or layers of pharmaceutically inert material will depend on a variety of factors, including the particular pharmaceutically active material utilized, and the desired release characteristics of the active ingredient in the final dosage form. Preferred materials include excipients and/or diluents having a granular nature, such that the pharmaceutically inert materials will effectively carry the pharmaceutically active material through the static mixer and provide a degree of abrasivity that helps prevent the pharmaceutically active material from adhering to process equipment surfaces in the hopper and static mixer. Preferred inert materials for preparing the layer or layers of pharmaceutically inert particulate material include those consisting of, consisting essentially of, or comprising dextrates.

It has been found that the dimensions of the hopper can affect the effectiveness of the process, especially the extent to which adherence of the active material to process equipment surfaces is reduced. Preferably, for a typical hopper having a cylindrical upper portion and a frustoconical lower portion, a suitable ratio of the diameter of the cylindrical section to the height of the cylindrical section is from about 1:1.2 to about 1:2.4.

The following examples are illustrative of the invention, but may include features that are not essential to operability of the invention. Accordingly, the examples do not limit the scope of the invention as defined by the appending claims.

Example 1

The process of the invention is evaluated using a dispensing hopper made of coated sheet metal having a 10 inch diameter with a 19 inch side wall, a 45 degree cone, and a 2 inch discharge. The dispensing hopper is attached to a 2 inch, six element plastic static mixer (Ross Engineering, Anderson, S.C.). Loperamide hydrochloride (0.533 kilograms) is layered between portions of dextrates, hydrated USP/NF (13 kilogram—Emdex® JRS Pharma, Highland Mills, N.Y.). The layers of loperamide hydrochloride and dextrates are discharged directly into a GMX-150 mixer/granulator (Vector Corporation, Marion, Iowa) and combined with other ingredients, then granulated with water. The granulation is combined with other ingredients and compressed into tablets. Analysis of the granulations, tablet mixes and compressed tablets demonstrates acceptable uniformity of the drug without loss of potency, and indicates that adhesion of loperamide hydrochloride to process equipment surfaces is minimized.

Example 2

The process is scaled up from a 50 kilogram pilot scale to a 165 kilogram production batch. A stainless steel hopper is fabricated with a 15 inch diameter, 36 inch high sidewall, 55 degree cone, and a 3 inch discharge. This hopper is attached to a 3 inch, nine element stainless steel static mixer (Ross Engineering, Anderson, S.C.). The loperamide hydrochloride (2.2 kilograms) is layered between portions (layers) of dextrates (30 kilograms) and is discharged through a static mixer directly into a Gral-600 mixer/granulator (Niro, Inc., Hudson, Wis.). The granulation is combined with other ingredients and compressed into tablets.

The following table shows the manufacturing process utilizing the static mixer.

|  | 40 kg batch | 165 kg batch |
| --- | --- | --- |
| Static Mixer |  |  |
| Dextrates Layer | 3 kg | 10 kg |
| Loperamide Hydrochloride Layer | 0.266 kg | 1.1 kg |
| Dextrates Layer | 3 kg | 10 kg |
| Loperamide Hydrochloride Layer | 0.267 kg | 1.1 kg |
| Dextrates Layer | 5 kg | 10 kg |
| Granulation |  |  |
| Dextrates | 5 kg | 63.2 kg |
| Discharge Static Mixer into Granulator | GMX-150 | Gral-600 |

-continued

|  | 40 kg batch | 165 kg batch |
|---|---|---|
| Dextrates | 15.6 kg | 45.4 kg |
| Starch, Pregelatinized (Binder) | 0.4 kg | 1.65 kg |
| Sodium Starch Glycolate (Disintegrant) | 3.467 kg | 14.3 kg |
| Microcrystalline Cellulose | 2 kg | 8.25 kg |
| Purified Water | 5.5 kg | 22 kg |

The dextrates are a free-flowing granular powder with a median particle size of about 300 microns. The dextrates perform well at carrying the loperamide hydrochloride, which is a fine powder. The dextrates also help keep the loperamide hydrochloride from adhering to surfaces of the static mixer. In addition to dextrates, other granular, free-flowing powder materials are preferred diluents/excipients for the process of this invention. As the particle size of the diluent become smaller, the carrying capacity for a fine powder, the flow properties, and the ability to completely discharge from the static mixer, will decrease, reducing the efficiency of the process. The utility of the invention is demonstrated by dispersing a drug into an excipient which is then incorporated into a granulation.

The invention is not limited to dispersing a drug for a granulation as shown in the example. The invention is also expected to provide benefits if the layered drug/excipient is discharged through a static mixer and then incorporated into a powder mix. The mixes from either method could be further processed into typical dosage forms, such as tablets, capsules or sachets.

A 2 inch static mixer with six mixing elements and a 3 inch static mixer with nine mixing elements achieve efficient distribution of a low dose drug, such as loperamide hydrochloride, into inert ingredients (e.g., excipients/diluents). The size and number of mixing elements may be varied depending on the drug and diluent. Static mixers constructed of stainless steel and/or plastic may be used in practicing the process of this invention. However, other materials may also be suitable.

The above description is considered that of the preferred embodiment only. Modifications of the invention will occur to those skilled in the art and to those who make or use the invention. Therefore, it is understood that the embodiment described above is merely for illustrative purposes and not intended to limit the scope of the invention, which is defined by the following claims as interpreted according to the principles of patent law, including the doctrine of equivalents.

The invention claimed is:

1. A process for distributing a pharmaceutically active particulate material in a pharmaceutically inert particulate material, comprising:
    (a) providing a first layer of a pharmaceutically inert particulate material;
    (b) disposing a layer of a pharmaceutically active particulate material on the first layer of pharmaceutically inert particulate material;
    (c) passing the layers of particulate material through a static mixer; and
    (d) discharging a blended mixture of a pharmaceutically active particulate material and a pharmaceutically inert particulate material.

2. The process of claim 1, wherein the pharmaceutically active particulate material is loperamide.

3. The process of claim 1, wherein the pharmaceutically active particulate material is a high potency drug administered in a therapeutically effective amount of 50 milligrams or less.

4. The process of claim 1, wherein the pharmaceutically active particulate material is a high potency drug administered in a therapeutically effective amount of 20 milligrams or less.

5. The process of claim 1, wherein the pharmaceutically active particulate material is a high potency drug administered in a therapeutically effective amount of 10 milligrams or less.

6. The process of claim 1, wherein the pharmaceutically active particulate material is a high potency drug administered in a therapeutically effective amount of 5 milligrams or less.

7. The process of claim 1, wherein the pharmaceutically active particulate material is a high potency drug administered in a therapeutically effective amount of 2 milligrams or less.

8. The process of claim 1, wherein the weight ratio of pharmaceutically inert particulate material in one layer to the pharmaceutically active particulate material in an adjacent layer is from about 5:1 to about 50:1.

9. The process of claim 1, wherein the weight ratio of pharmaceutically inert particulate material in one layer to the pharmaceutically active particulate material in an adjacent layer is from about 5:1 to about 20:1.

10. The process of claim 1, wherein steps (a) and (b) are repeated a plurality of times to form alternating layers of pharmaceutically active material and pharmaceutically inert material.

11. The process of claim 10, wherein the plurality of layers are deposited in a dispensing hopper attached to the static mixer.

12. The process of claim 11, wherein the hopper has a cylindrical upper section with a circular cross section, and wherein a ratio of diameter to height of the cylindrical section of the hopper is from about 1:1.2 to about 1:2.4.

13. The process of claim 1, wherein the pharmaceutically inert material comprises dextrates.

14. A process for making a pharmaceutical granulation, comprising:
    (a) providing a first layer of a pharmaceutically inert particulate material;
    (b) disposing a layer of a pharmaceutically active particulate material on the first layer of pharmaceutically inert particulate material;
    (c) passing the layers of particulate material through a static mixer;
    (d) discharging a blended mixture of a pharmaceutically active particulate material and a pharmaceutically inert particulate material, and
    (e) combining and granulating the blended mixture with additional particulate material.

15. The process of claim 14, wherein the pharmaceutically active particulate material is loperamide.

16. The process of claim 14, wherein the pharmaceutically active particulate material is a high potency drug administered in a therapeutically effective amount of less than 50 milligrams.

17. A process for making a pharmaceutical tablet, comprising:
    (a) providing a first layer of a pharmaceutically inert particulate material;
    (b) disposing a layer of a pharmaceutically active particulate material on the first layer of pharmaceutically inert particulate material;
    (c) passing the layers of particulate material through a static mixer;

(d) discharging a blended mixture of a pharmaceutically active particulate material and a pharmaceutically inert particulate material;
(e) combining and granulating the blended mixture with additional particulate material to form a granulation, and
(f) compressing the granulation to form a tablet.

18. The process of claim 17, wherein the pharmaceutically active particulate material is loperamide hydrochloride, the pharmaceutically inert particulate material comprises dextrates, and wherein the dextrates and loperamide hydrochloride are arranged in alternating layers in which the weight ratio of the pharmaceutically inert particulate material in one layer to the pharmaceutically active particulate material in an adjacent layer is from about 5:1 to about 50:1.

19. The process of claim 17, wherein the pharmaceutically active particulate material is loperamide hydrochloride, the pharmaceutically inert particulate material comprises dextrates, and wherein the dextrates and loperamide hydrochloride are arranged in alternating layers in which the weight ratio of the pharmaceutically inert particulate material in one layer to the pharmaceutically active particulate material in an adjacent layer is from about 5:1 to about 20:1.

20. The process of claim 19, wherein the additional particulate materials comprise dextrates, a tablet binder, and at least one disintegrant.

\* \* \* \* \*